United States Patent [19]

Wandrey et al.

[11] 4,304,858

[45] Dec. 8, 1981

[54] PROCESS FOR THE CONTINUOUS ENZYMATIC CHANGE OF WATER SOLUBLE α-KETOCARBOXYLIC ACIDS INTO THE CORRESPONDING AMINO ACIDS

[75] Inventors: Christian Wandrey; Rolf Wichmann, both of Jülich; Wolfgang Leuchtenberger, Bruchköbel; Maria-Regina Kula, Wolfenbüttel; Andreas Bückmann, Braunschweig-Stöckheim, all of Fed. Rep. of Germany

[73] Assignee: Degussa Aktiengesellschaft, Frankfurt, Fed. Rep. of Germany

[21] Appl. No.: 172,446

[22] Filed: Jul. 25, 1980

[30] Foreign Application Priority Data

Jul. 25, 1979 [DE] Fed. Rep. of Germany ....... 2930070

[51] Int. Cl.³ .................... C12P 13/04; C12P 13/08; C12P 13/06
[52] U.S. Cl. .................................. 435/115; 435/106; 435/116; 435/288; 435/813
[58] Field of Search ............... 435/106, 115, 116, 288, 435/813

[56] References Cited

U.S. PATENT DOCUMENTS 3,183,170  5/1965  Kitai et al. ................. 435/116 X
4,251,631  2/1981  Simon ........................ 435/106

OTHER PUBLICATIONS

Cuatrecanas, Journal of Biological Chemistry, vol. 245, pp. 3059–3065 (1970).

*Primary Examiner*—Lionel M. Shapiro
*Attorney, Agent, or Firm*—Cushman, Darby & Cushman

[57] ABSTRACT

Water soluble α-ketocarboxylic acids are continuously converted in a membrane reactor into the corresponding aminoacids. The conversion takes place in the presence of a substrate specific dehydrogenase, of ammonium ions and of a nicotinamide-adenine-dinucleotide (NAD+/NADH) enlarged in molecular weight through linkage to a water soluble polymer as coenzyme. Simultaneously NADH is regenerated continuously from NAD+ in presence of a formate dehydrogenase and from formate ion. The membrane must have a mean pore diameter of 1 to 3 nm. As coenzyme there is employed 0.1 to 10 mmol/l of NAD+/NADH present bound to a polyoxyethylene having an average molecular weight between 500 and 50,000. There is continuously supplied to the reactor a substrate stream which contains 50 to 100% of the maximum amount soluble, but not over 2,000 mmol/l, of the reacting α-ketocarboxylic acid in the form of a water soluble salt, an ammonium ion in an amount about equimolar to the amount of substrate and 100 to 6,000 mmol/l of a formate. There is maintained over the membrane a differential pressure of 0.1 to 15 bar. There is continuously drawn off behind the membrane a filtrate stream containing the aminoacid formed.

12 Claims, No Drawings

PROCESS FOR THE CONTINUOUS ENZYMATIC CHANGE OF WATER SOLUBLE α-KETOCARBOXYLIC ACIDS INTO THE CORRESPONDING AMINO ACIDS

BACKGROUND OF THE INVENTION

The invention is directed to a process for the continuous enzymatic conversion of water soluble α-ketocarboxylic acid into the corresponding amino acid in the presence of a substrate specific dehydrogenase, ammonium ions and nicotinamide-adenine-dinucleotide (NAD+/NADH) of increased molecular weight by bonding to a water soluble polymer in a membrane reactor equipped with an ultrafiltration membrane with simultaneously regeneration of NADH from NAD+ by means of formate ion in the presence of a formate dehydrogenase.

Enzymatic conversions in membrane reactors indeed have been investigated for a long time but customarily without forced convection of the reaction mixture over the membrane without continuous regeneration of a coenzyme and with very small substrate concentrations. The use of such conversions on a production scale suffered because previously continuous carrying out of the process was not possible and there could only be obtained small space-time-yields.

SUMMARY OF THE INVENTION

The process of the invention comprises employing a membrane reactor, the membrane of which has a mean pore diameter of 1 to 3 nm and which contains a solution of the formate dehydrogenase, the substrate specific dehydrogenase and from 0.1 to 10 mmol/l of NAD+/NADH present bound to a polyoxyethylene having an average molecular weight between 500 and 50,000, continuously supplying an aqueous solution having 50 to 100% of the maximum amount soluble, but not over 2,000 mmol/l, the α-ketocarboxylic acid to be converted in the form of a water soluble salt as substrate an amount of ammonium ion about equimolar to the substrate amount, and from 100 to 6,000 mmol/l of a formate, maintaining a differential pressure over the membrane of 0.1 to 15 bar and continuously drawing off behind the membrane a filtrate stream containing the aminoacid formed.

The process of the invention permits water soluble α-ketocarboxylic acids to be converted continuously and with high space-time-yields into the corresponding aminocarboxylic acids and is therefore useful for a cost favorable production of these aminoacids.

As reaction vessel there is used an ultrafiltration membrane which membrane serves to retain in the reactor the enzyme employed and the necessary coenzyme for the conversion, but permits the lower molecular weight product and the unconverted substrate to pass through. The membrane reactor can also be formed as a so-called flat membrane reactor. In this type of reactor, for example, it can be a flat cylindrical vessel on which there is placed a cover made tight by means of an O-ring. The relatively stretched flat membrane is attached together with the O-ring. The substrate stream is supplied by a metering pump to the reaction space lying below the membrane, which reactor space is suitably equipped with a stirring device, e.g., a magnetic stirrer. The filtrate stream containing the product leaves the reaction space through the membrane and a plate provided with bores for the purpose of avoiding its mechanical stresses and is drawn off out of the cover. A so-called hollow fiber-membrane reactor, in which a hollow fiber bundle made of ultrafiltration membranes, a so-called hollow fiber module, at the place the flat membrane enters is then advantageous if because of the geometric arranged there are to be attained higher Reynolds numbers of the fluid parallel to the membrane and therewith lower coating of the membrane with enzyme proteins. In this type of reactor, for example, it is a matter of a type of loop reactor, which consists of a reaction container, a circulation pump and the hollow fiber module. The substrate stream is supplied to the reaction container by means of a metering pump. In this the reaction mixture is pumped around whereby the pumped around stream is in the proportion to the substrate stream at least about 100:1, in order to keep the coating of the hollow fiber membranes with enzyme protein as small as possible. The filtrate stream containing the product passes through the hollow fiber membranes and is collected behind these and drawn off. There are used for the process of the invention membranes which have a mean pore diameter of 1 to 3 nm. Suitable materials for the membranes, for example, are acetyl celluloses, polyamides, e.g., nylon-6,6, polysulfones or modified polyvinyl alcohols.

The membrane reactor contains a solution of a formate dehydrogenase, a substrate specific dehydrogenase and NAD+/NADH greatly enlarged in molecular weight. The formate dehydrogenase is suitably employed in such an amount that its activity is at least 12,000 $\mu$mol/l·minute. Upwardly the amount of its addition suitably should be so limited that the protein concentration is maximally about 20 g/l. The substrate specific dehydrogenase is suitably added in such an amount that the ratio of the activities of formate dehydrogenase and substrate specific dehydrogenase is between 1:1 and 1:5.

The required NAD+/NADH as coenzyme in the process of the invention must be enlarged to such an extent in molecular weight through bonding to a polyoxyethylene that it is indeed still water soluble in order to permit a homogeneous catalysis, on the other hand, however, together with the two enzymes to be safely held back by the membrane. For this purpose, for example, the coenzyme is first converted in its oxidized form with ethylenimine to the N(1)-aminoethyl derivative, which then on its part is coupled to a carboxylated polyethyleneglycol with the aid of the carbodiimide method (see Cuatrecanas, J. Biol. Chem, Volume 245, page 3059 (1970)). These polyoxyethylenes have an average molecular weight between 500 and 50,000, preferably between 1,200 and 10,000. The coupled product obtained is then reduced to the corresponding NADH derivative, through a Dimroth-arrangement converted into the N(6)-derivative and in a given case again oxidized to the corresponding NAD+-derivative. The coenzyme having an enlarged molecular weight is added in such an amount that the concentration of NAD+/NADH is 0.1 to 10 mmol/l, preferably 1 to 7 mmol/l.

The membrane reactor is continuously supplied with an aqueous solution of the substrate, ammonium ions and formate ions. The concentration of the substrate should amount to 50 to 100% of the maximal possible concentration, however, it is not permitted to exceed 2,000 mmol/l, preferably not over 1,000 mmol/l. The concentration of ammonium ions must be equimolar to the amount of substrate for a complete conversion of the substrate, an excess of ammonium ions, however, does not disturb the reaction. On the other hand, however, on account of the forced remixing between product and substrate before the membrane in the process of the invention there cannot be attained besides a quantitative conversion. In many cases therefore it suffices if the ammonium ion is employed in a certain deficiency, for example, only with about 80% of the amount required for a quantitative conversion of the substrate. The concentration of formate ions is between 100 and 6,000 mmol/l, preferably between 300 and 2,000 mmol/l. As formates there are preferably used sodium or potassium formate. However, it is particularly advantageous if the substrate solution being supplied. The ammonium ions and the formate ion are added together in the form of ammonium formate.

During the conversion there must be maintained over the membrane a pressure differential of 0.1 to 15 bar, preferably 0.2 to 3 bar, which is attained by use of a correspondingly dimensioned metering pump for the substrate solution being supplied and in a given case through a butterfly valve in the filtrate stream behind the membrane. The pressure differential causes a filtrate stream to pass through the membrane with the desired velocity. The absolute pressure on the delivery side of the membrane should suitably be so adjusted that even with powerful stirring or repumping into the reaction space before the membrane for production of a strong turbulence along the membrane and therewith for the avoidance of a coating of the membrane with the enzyme or the coenzyme of increased molecular weight the pressure at no place is reduced to such an extent that there is a degassing of the reaction mixture on the delivery side. The membrane reactor is maintained at a customary temperature between 25° and 50° C. for enzymatic conversions. Likewise the pH of the reaction mixture during the conversion is maintained in the customary range of 5 to 9 enzymatic conversions.

Suitable formate dehydrogenases for carrying out the process of the invention can be isolated, for example, from *Candida boidinii* or from *Pseudomonas oxalaticus*. An example of a substrate specific dehydrogenase usable in the process of the invention is the frequently employed L-alanine dehydrogenase which can be obtained from *Bacillus subtilis*. With their help, for example, pyruvic acid can be converted into L-alanine, 2-oxo-4-methylvaleric acid into L-leucine, 2-oxo-3-methylvaleric acid into L-isoleucine, 2-oxo-3-methylbutyric acid into L-valine or 2-oxo-valeric acid into L-norvaline. Suitably the reacting α-ketocarboxylic acids are employed in the form of their sodium or potassium salts, e.g., sodium pyruvate or potassium 2-oxo-valerate. Since in the conversion of α-ketocarboxylic acids, e.g., α-ketoalkanoic acids into the corresponding aminoacids, e.g., aminoalkanoic acids an optically active center is newly formed, the product concentration in the filtrate stream can be measured continuously with the help of a polarimeter. The aminoacid formed can be obtained from the filtrate in known manner, e.g., with the help of an acidic ion-exchanger.

The process can comprise, consist essentially of or consist of the steps set forth and the material employed can comprise, consist essentially of or consist of those stated.

Unless otherwise indicated all parts and percentages are by weight.

In the following examples the process of the invention will be explained in more detail in connection with the conversion of sodium pyruvate into L-alanine.

DETAILED DESCRIPTION OF THE INVENTION

Example 1

A flat membrane reactor maintained at a temperature of 40° C. and having a volume of 10 ml which was equipped with a magnetic stirrer and an ultrafiltration membrane having a diameter of 62 mm with a nominal exclusion limit of 5,000 (supplier: Amicon, Witten; Type DM 5), for sterilization was rinsed well with an aqueous formaldehyde solution for about 5 hours with the help of a metering pump adjusted to a conveying velocity of 20 ml/hours. Subsequently during about a further 5 hours the formaldehyde solution was displaced by distilled water. Then there was supplied, likewise with a conveying speed of 20 ml/hour for about 2.5 hours a substrate solution filtered over a sterile filter (0.2). The substrate solution contained 500 mmol/l of sodium pyruvate, 400 mmol/l of ammonium formate and 50 mmol/l of sodium dihydrogene phosphate, which solution was adjusted to pH 8 with sodium hydroxide solution. Then in place of the substrate solution there were metered in 10 ml of a coenzyme solution, which contained 3.66 mmol/l NADH bonded to a polyoxyethylene with a mean molecular weight of 10,000 and 50 mmol/l of a phosphate buffer to maintain a pH of 8. After the complete addition of the coenzyme solution there was again supplied the above substrate solution with a conveying speed of 20 ml/hour. Then there was added to the reaction space before the membrane through a lateral bore by means of an injector 100 mg of formate hydrogenase (activity 6.74 $\mu$mol/mg$\times$minute with formate as substrate, 40° C. and pH 8) in the form of an aqueous glycerine solution (50 weight percent glycerine; 10 mg formate dehydrogenase/ml) and 1.6 mg L-alanine dehydrogenase (activity 415 $\mu$mol/mg$\times$minute with pyruvate as substrate, 40° C. (and pH 8) in the form of an aqueous ammonium sulfate solution (2.4 mol/l $(NH_4)_2SO_4$; 5 mg L-alanine dehydrogenase/ml). At the control selected the ratio of the activities of formate dehydrogenase and L-alanine dehydrogenase was 1:1. The conversion was followed continuously with the help of a polarimeter flow cell constructed in the filtrate stream. The pressure differential over the membrane at the beginning amounted to 0.2 bar, increased gradually to 0.5 bar and then remained constant. Within an operating time of, in all, about 50 hours there were obtained 175 mmol of L-alanine. The maximum rate of conversion was 6.45 mmol of L-alanine/hour.

The yield was 108 mmol of L-alanine based on 1 mg L-alanine dehydrogenase, or 1.75 mmol of L-alanine, based on 1 mg of formate dehydrogenase.

Example 2

The sterilization of the 10 ml flat membrane reactor (membrane with a nominal exclusion limit of 5,000; supplier: Amicon, Witten; Type YM 5) which was held at a temperature of 25° C. took place as in Example 1.

A sterile filtrated solution was then supplied for about 2.5 hours with a conveying velocity of 20 ml/hour. The sterile filtrated solution contained 400 mmol/l of sodium pyruvate, 400 mmol/l of ammonium formate and 50 mmol/l of sodium dihydrogen phosphate and was adjusted to a pH of 8 with aqueous sodium hydroxide. Subsequently in place of the substrate there was supplied at a conveying velocity of 4 ml/hour a mixture of 7 ml of the coenzyme solution according to Example 1 and 138 mg of formate dehydrogenase (activity 0.85 $\mu$mol/mg$\times$minute with formate as the substrate at 25° C. and pH 8) in the form of an aqueous glycerine solution (50 weight percent glycerine; 10 mg formate dehydrogenase/ml). Then there were supplied to the reaction space through a lateral bore by means of an injector 2.78 mg of L-alanine dehydrogenase (activity 233 $\mu$mol/mg$\times$minute with pyruvate (sodium pyruvate as substrate, 25° C. and pH 8) in the form of an aqueous ammonium sulfate solution (2.5 mol/l $(NH_4)_2SO_4$; 5 mg L-alanine dehydrogenase/ml). The ratio of the activities of formate dehydrogenase and L-alanine dehydrogenase consequently was 1:4. There were obtained 48 mmol/L-alanine within an operating time of 59 hours, corresponding to a yield of 17.3 mmol of L-alanine, based on 1 mg L-alanine or 0.35 mmol of L-alanine based on 1 mg L-alanine dehydrogenate, or 0.35 mmol L-alanine based on 1 mg of formate dehydrogenate.

Example 3

The sterilization of the 10 ml flat membrane reactor (membrane with a noninal: Amicon Type YM 5) which was held to a temperature of 25° C. took place as in Example 1.

Then for about 2.5 hours there was supplied at a conveyor speed of 20 ml/hour a sterile filtrated solution which contained 400 mmol/l of sodium pyruvate, 800 mmol/l of ammonium formate and 50 mmol/l of sodium dihydrogen phosphate and sodium hydroxide to adjust the pH to 8. Subsequently in place of the substrate solution having a conveyor speed of 4 ml/hour there was supplied a mixture of 10 ml of the coenzyme according to Example 1 and from 85 mg formate dehydrogenase (activity 0.85 $\mu$mol/mg$\times$minute with formate as substrate, 25° C. and pH 8) in the form of an aqueous glycerine solution (50 weight percent glyerine; 10 mg formate dehydrogenase/ml). Then there were added to the reaction space through a lateral bore by means of an injector 0.94 mg of L-alanine dehydrogenase (activity 233 $\mu$mol/mg$\times$minute with pyruvate as the substrate, 25° C. and pH 8) in the form of an aqueous ammonium sulfate solution (2.4 mol/l of $(NH_4)_2SO_4$; 5 mg L-alanine dehydrogenase/ml). The ratio of the activities therefore amounted to 1:2.2. Within an operating time of 140 hours there were obtained 92 mmol of L-alanine, corresponding to a yield of 98 mmol of L-alanine based on 1 mg L-alanine dehydrogenase or 1.08 mmol of L-alanine, based on 1 mg of formate dehydrogenase.

What is claimed is:

1. A process for continuously enzymatically converting water soluble $\alpha$-ketocarboxylic acids in a membrane reactor equipped with an ultrafiltration membrane into the corresponding aminoacids comprising carrying out the conversion in the presence of a substrate specific dehydrogenase, of ammonium ions and of a nicotinamide-adenine-dinucleotide (NAD$^+$/NADH) of increased moecular weight through linkage to a water soluble polymer as coenzyme while simultaneously regenerating NADH from NAD$^+$ in presence of a formate dehydrogenase by means of formate ion, said membrane having a mean pore diameter of 1 to 3 nm, there being employed as coenzyme 0.1 to 10 mmol/l of NAD$^+$/NADH bound to a polyoxyethylene having an average molecular weight between 500 and 50,000, continuously supplying to the reactor a substrate stream which contains 50 to 100% of the maximum amount soluble, but not over 2,000 mmol/l, of the reacting $\alpha$-ketocarboxylic acid in the form of a water soluble salt as substrate, an ammonium ion in an amount about equimolar to the amount of substrate and 100 to 6,000 mmol/l of a formate, maintaining over the membrane a differential pressure of 0.1 to 15 bar and continuously drawing off behind the membrane a filtrate stream containing the aminoacid formed.

2. A process according to claim 1 wherein the formate dehydrogenase and the substrate specific dehydrogenase are added in an amount such that the ratio of their activities is between 1:1 and 1:5.

3. A process according to claim 2 wherein the substrate solution which supplied the ammonium ions and the formate ions as ammonium formate.

4. A process according to claim 1 wherein the substrate the ammonium ions and the formate ions as ammonium formate.

5. A process according to claim 1 wherein the substrate stream contains not over 1,000 mmol/l of the ketocarboxlic.

6. A process according to claim 5 wherein the formula is present in an amount of 300 to 2,000 mmol/l.

7. A process according to claim 6 wherein the pressure is 0.2 to 3 bar.

8. A process according to claim 7 wherein the ketocarboxylic acid salt is a salt of pyruvic acid, 2-oxo-4-methylvaleric acid, 2-oxo-3-methylvaleric acid, 2-oxo-3-methylbutyric acid or 2-oxovaleric acid.

9. A process according to claim 1 wherein the ketocarboxylic acid salt is a salt of pyruvic acid, 2-oxo-4-methylvaleric acid, 2-oxo-3-methylvaleric acid, 2-oxo-3-methylbutyric acid or 2-oxovaleric acid.

10. A process according to claim 8 wherein the ketocarboxylic acid is pyruvic acid.

11. A process according to claim 10 wherein the substrate specific dehydrogenase is L-alanine dehydrogenase.

12. A process according to claim 11 wherein the salt is a sodium or potassium salt.

* * * * *